United States Patent [19]

Dursch

[11] 4,016,222

[45] Apr. 5, 1977

[54] UNSATURATED PHOSPHORUS COMPOUNDS

[75] Inventor: Walter Dursch, Konigstein, Taunus, Germany

[73] Assignee: Hoechst Aktiengesellschaft, Frankfurt am Main, Germany

[22] Filed: Oct. 14, 1975

[21] Appl. No.: 622,264

[30] Foreign Application Priority Data

Oct. 19, 1974 Germany .......................... 2449733

[52] U.S. Cl. .............................. 260/932; 260/940; 260/941; 260/942; 260/943; 260/952; 428/276

[51] Int. Cl.² .......................................... G07F 9/40

[58] Field of Search .......... 260/952, 932, 940, 941, 260/943, 942

[56] References Cited

UNITED STATES PATENTS 2,806,828 9/1957 Hardman ....................... 260/952 X
3,886,236 5/1975 D'Alelio ............................ 260/952

FOREIGN PATENTS OR APPLICATIONS 47-29490 2/1972 Japan ................................ 260/952

Primary Examiner—Richard L. Raymond
Attorney, Agent, or Firm—Connolly and Hutz

[57] ABSTRACT

Phosphorus organic compounds obtained by reacting phosphinic acids or phosphinic acid halides with a (meth)acrylic acid glycidylester. The compounds thus obtained can be polymerised and are useful for making textile fibers flame-proof.

3 Claims, No Drawings

UNSATURATED PHOSPHORUS COMPOUNDS

The present invention relates to unsaturated phosphorus compounds, a process for preparing them and their use as flameproof finishing agents.

It is known that monomers to which the constitution

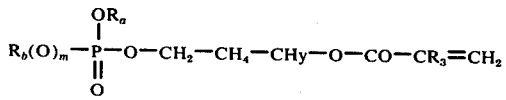

has been attributed can be prepared from compounds of the formulae

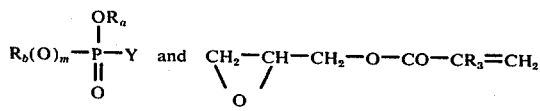

in which formulae $m$ stads for zero or 1, Y for chlorine or bromine, $R_a$ for a saturated hydrocarbon radical which may also carry chlorine or bromine atoms, $R_b$ has the same meaning as $R_a$ but additionally stands for aryl, if $m$ is zero (see German Auslegeschrift No. 1,148,751 and German Patent No. 1,050,760). These above-cited monomers are being used for the flameproof finishing of plastics.

The present invention provides acrylic acid esters containing phosphinic acid ester groups, and mixtures thereof, which correspond to the general formulae

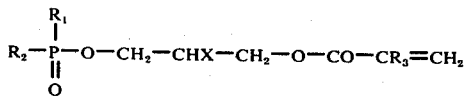

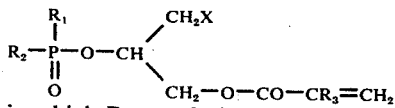

in which $R_1$ stands for a saturated or unsaturated aliphatic hydrocarbon radical having 1 to 8, preferably 1 to 4, carbon atoms, which may also carry chlorine or bromine atoms, the nitrile group or the groups —$OR_4$, —$COOR_4$ or —$CON(R_4)_2$, $R_2$ has the same meaning as $R_1$ and addtionally stands for a radical of the formulae

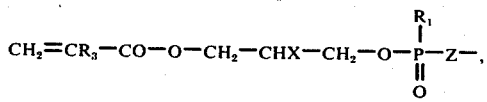

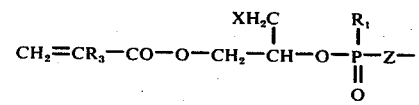

or

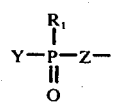

in which Z stands for a straight-chained or branched alkylene group having 1 to 8 carbon atoms, preferably 1 to 3 carbon atoms, or the phenylene group or a xylylene group, preferably p-xylylene, which may carry chlorine or bromine atoms or hydroxy groups, and Y stands for a straight-chained or branched -0-alkyl group having 2 to 8, preferably 2 to 4, carbon atoms, which may also carry chlorine or bromine atoms and/or hydroxy groups, or for chlorine, bromine or hydroxy, $R_3$ stands for hydrogen or methyl, $R_4$ for hydrogen, alkyl of 1 to 8, preferably 1 to 4, carbon atoms, or an alkenyl radical having 2 to 8, preferably 2 to 4, carbon atoms, which may carry chlorine or bromine atoms or hydroxy groups, and X stands for chlorine, bromine or hydroxy.

The present invention further provides a process for preparing these compounds, wherein (a) 1 mol of a compound of the formula

is reacted with 0.98 to 2 mols of a (meth)acrylic acid glycidyl ester of the formula

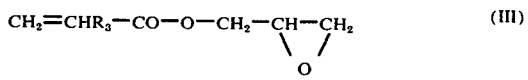

(b) 1 mol of a compound of the formula

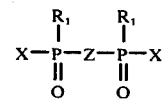

is reacted with 1.95 to 4 mols of a (meth)acrylic acid glycidyl ester, or (c) 1 mol of a compound of the formula

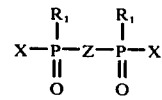

is reacted with 1 to 1.95 mols of a (meth)acrylic acid glycidyl ester, and optionally with 0.1 to 2 mols of an alkylene oxide of the formula

in which $R_1$, $R_3$, X and Z are defined as above, and $R_6$ stands for hydrogen, a chloromethyl group or an alkyl group of 1 to 6 carbon atoms. This reaction may also be carried out in an inert solvent or diluent.

As compounds of formula II, there may be mentioned, if X stands for hyroxy, the following compounds, for example, diethyl phosphinic acid, dipropyl phosphinic acid, diisobutyl phosphinic acid, n-hexyl-methyl phosphinic acid, n-octyl-methyl phosphinic acid, chloromethyl-methyl phosphinic acid, bis-chloromethyl phosphinic acid, chloroethyl-methyl phosphinic acid, methyl-vinl phosphinic acid, allyl-methyl phosphinic acid, 1-bromo-vinyl phosphinic acid, 2-bromo-allyl phosphinic acid, 2-methoxy-ethyl-methyl phosphinic acid, 2-cyanoethyl-methyl phosphinic acid, 2-methoxycarbonyl-ethyl-methyl phosphinic acid, 2-dimethylamino-carbonylethyl-methyl phosphinic acid, 2-carboxyethyl-methyl phosphinic acid, ethane-1,2-bis(methyl-phosphinic acid)mono-2-hydroxy-ethyl ester, phenylene-1,4-bis-methyl phosphinic acid, xylylene-1,4-bis-methyl phosphinic acid or -mono-2-hydroxy-propyl ester, and preferably, owing to their high content of phosphorus and relatively easy accessability, phosphinic acids whose alkyl groups contain a total of 1 to 4 carbon atoms, such as dimethyl phosphinic acid, ethylmethyl phosphinic acid and methylpropyl phosphinic acid.

Moreover, the chlorides and bromides of all the above-cited phosphinic acids are suitable. In this case, X stands for chlorine or bromine. Preferably used are chlorides of the three last-mentioned phosphinic acids. The reaction components may be used in about stoichiometric amounts. An excess amount of glycidyl ester, preferably of up to 20%, which May be distilled off, has proved to be advantageous in most cases. The most adequate molar ratio of substances III to substances II therefore ranges from 0.98 to 2 : 1, preferably from 1.02 to 1.2 : 1, when the phosphorus compound is a monofunctional substance which can fix only one molecule of compound III (preferably a phosphorus atom per molecule); or when it is a bifunctional compound capable of fixing two molecules of substance III, the molar ratio chosen ranges from 1.95 to 4.0 : 1, preferably from 2.05 to 2.3 : 1 (variant b).

Since satisfactory use can be made of the substances of the invention, i.e. their polymerization can be brought about with the desired degree of crosslinking, when only part of the monomers used contains two acrylic acid radicals, the use of the above-mentioned bifunctional compounds allows even a smaller amount of (meth)acrylic acid glycidyl ester of formula III to be employed, for example 1 to 1.95 moles of (meth)acrylic acid glycidyl ester per mol of bifunctional phosphorus compound, preferably 1.1 to 1.4 mols. The unreacted reactive groups P-X are then converted into neutral phosphinic acid ester groups by reacting them with alkylene oxides as described sub (c).

The reaction temperatures range from 0° to 150° C, preferably from about 30° to 120° C. In the case of X standing for chlorine or bromine, they may be maintained at the lower portion of the temperature range of from about 40° to 90° C, of 0.1 to 3%, preferably 0.2 to 1%, of a halide, preferably a chloride or bromide, of titanium, zirconium, aluminium or tin is added as a catalyst. The addition of a catalyst is, however, not compulsory.

To prevent polymerization of the acrylic or methacrylic acid esters during the reaction, substances that inhibit polymerization, as known for acrylic esters, for example hydroquinone, hydroquinone monomethyl ether, copper chips, phenothiazine or methylene blue, have to be present in the reaction mixture.

The process of the invention is generally carried out by heating the phosphorus compound, optionally with the addition of a polymerization inhibitor and/or a metal salt catalyst as disclosed above, to the reaction temperature and adding the glycidyl ester, while stirring and maintaining the reaction temperature by dissipating the reaction heat, and then continuing to stir until the acid number (mg of KOH per g of crude product) remains constant, desirably at a value below 10. A remaining acidity may be neutralised by a treatment with the alkylene oxides of formula IV of formula IV or by careful neutralization with alkaline agents, for example a methanolic sodium methylate solution. Salt precipitates, if any, are suction-filtered, where required after dilution with an organic solvent. If the glycidyl esters have been used in excess, they can be distilled off in vacuo, especially if X stands for chlorine, after evaporation of the solent that may have been used. The prepurified residues thus obtained can be used directly for the purpose of flame-proof finishing of fibrous material.

The reaction may also be carried out in a solvent but this is generally not necesssary.

Suitable solvents are aromatic hydrocarbons, for example, benzene, toluene, xylene; aliphatic chlorohydrocarbons, for example methylene chloride, chloroform or carbon tetrachloride; aromatic chlorohydrocarbons, for example chlorobenzene; dialkyl ethers, for example diethyl-, diisopropyl or di-n-butyl ether; or nitriles, for example acetonitrile.

In some cases, especially if X stands for chlorine, and $R_1$ and $R_2$ each for a lower unsubstituted alkyl group, it is possible further to purify the crude products by fractionated distillation.

The reaction products thus obtained are colorless to yellowish viscous oily sustances which polymerize in the presence of radical-yielding substances, preferably at elevated temperatures. Owing to their relatively high content of phosphorus, they are therefore outstandingly suitable for the preparation of flame-proof finishes on fibrous material, especially on synthetic fibrous material. The flame proofing of textile fibers is made by applying a solution of the compounds of formula Ia and Ib in an inert solvent such as water or alcohol on to the fiber material and polymerising them by using radicals. This process is detailed in German Patent application Serial Number P 24,49,465.3 and in the corresponding U.S. Pat. Application to which a Serial Number has not yet been alloted and which is hereby incorporated by reference.

According to the general formulation

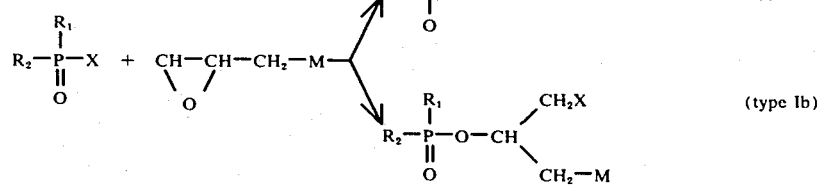

in which M stands for hydrogen or the radicals —O—CO—CR$_3$=CH$_2$, the process of the present invention provides a linear compound type Ia and/or branched type Ib. To differentiate these types, the infrared spectrum is not suitable, the characteristical differences are rather established by NMR spectra. For proper attribution of the bands, the distillable reaction product is prepared from ethylmethyl phosphinic acid chloride and propylene oxide (M=H). The second distillation yields a colorless oily substance having a refractive index $n_{20}$ of 1.4583, which contains, according to the gaseous-phase chromatogram, two compounds with percentages of 86 and 14%, their elution temperatures being close to each other. With the aid of the gaseous-phase preparative chromatography, it is possible to separate the two substances quantitatively. In the NMR spectrum, the main product having a somewhat lower elution temperature shows a characteristical double peak at $\delta = 3.7$ ppm and a multiple peak at $\delta = 4.7$ ppm, whereas the byproduct only shows one multiple peak at $\delta = 4.1$ ppm. The result shows that the main product is the branched type Ib, the double peak at $\delta = 3.7$ ppm corresponding to the $CH_2$ — group and the multiple peak at $\delta = 4.7$ ppm to the —CH— group. The by-product represents the linear type Ia, in which $\delta CH_2$ and $\delta CH$ at 4.1 ppm coincide on a multiple peak.

As for the unsaturated compounds that can be distilled or not and in which X is chlorine and M the group —O—CO—$CR_3$=$CH_2$, peaks which are characteristical for type Ib may be found at $\delta CH_2 = 3.8$ ppm and at $\delta CH = 4.8$ ppm and additionally a group of peaks at $\delta = 4.4$ ppm, which can be clearly attributed to the other —$CH_2$—group neighboring the (meth)acrylic acid radical. At $\delta = 4.1$ to 4.2 ppm, there are no, or only very weak, signals. This allows the conclusion that, if X is chlorine and M the group —O—CO—$CR_3$=$CH_2$, more than 90 % of the branched type Ib compounds are sure to be formed. The situation is a little more complicated when free phosphinic acids (X = OH) are used.

The reaction product of ethylmethyl phosphinic acid and excess propylene oxide (M=H) can be checked by means of gaseous phase chromatograms and NMR spectra taken of the crude product and of a product that has been purified by two fractionated distillations. The double fractionation permits a concentration of the main component from 80 to 98%, as the gaseous-phase chromatogram proves. However, only one peak is observed. In the NMR spectrum of the crude and of the purified products, the double peak that is characteristical of the —$CH_2$—group of the branched type Ib is distinct at $\delta = 3.6$ ppm and the multiple peak which is typical of the —CH— group is distinct at $\delta = 5.6$ ppm. However, there is another multiple peak corresponding to the linear type Ia to be seen in great intensity at $\delta = 4.0$ ppm. A quantitative evaluation shows that both the crude product and the product that has been purified by two-fold distillation contain the types Ia and Ib each in about the same percentage, i.e. the distillation does not cause a decisive shift between the types Ia and Ib. The elution temperatures of the two compounds are apparently so close to each other that they raise only one peak in the gaseous-phase chromatogram.

On the basis of the NMR spectra of the unsaturated compounds, which are generally not liable to distillation and in which X is OH and M is —O—CO—$CR_3$=$CH_2$, it can be assumed that the types Ia and Ib are also present in about the same proportions.

The following Examples illustrate the invention.

EXAMPLE 1

0.1 Gram of phenothiazine was dissolved at 75° C in 140.6 g (1 mol) of methyl-propyl phosphinic acid chloride. Within 120 minutes, 145 g (1.05 mols) of a commercial-type 92.8% acrylic acid glycidyl ester were then added dropwise. The reaction heat produced was dissipated by cooling with water of 25° C. After stirring had been continued for 5 hours at 90° C, the acid number had dropped to about 2. The reaction product was heated to 110° C at a reduced pressure of 0.05 torr, whereupon 34 g of excess acrylic acid glycidyl ester and byproducts were distilled off. 251 Grams of crude product were obtained, which corresponded to 93.4% of the theoretical yield. This product was suitable as such as a flame-proofing agent.

When 100 g of the crude product were distilled under a pressure of 0.05 torr via a Vigreux column, 25 cm in length, 79 g were recovered as a main fraction with a boiling point of 118° – 121° C under a pressure of 0.05 mmHg and a refractive index $n_{20} = 1.4726$. After repeated fractionation of this main fraction, the resulting main amount was 55 g having a boiling point, under 0.11 mm Hg, of 123° – 126° C and a refractive index $n_{20} = 1.4725$. This fraction contained 90.8 % of the compound of the formula

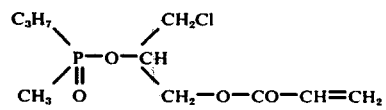

according to the NMR spectrum and the gaseous-phase chromatogram. The yield (calculated on the 100% compound) was 44.7% of the theoretical yield. The molecular weight of the 100% substance was 268.69.

EXAMPLE 2

75.6 Grams (0.6 mol) of ethyl-methyl phosphinic acid chloride and 0.1 g of phenothiazine were heated to 105° C, and within 90 minutes, 82.8 g (0.6 mol) of a commercial-type 92.8% acrylic acid glycidyl ester were added dropwise while cooling. After stirring had been continued for 4 hours, the acid number had dropped to 8.7. Under a pressure of 0.05 torr, 22 g of volatile parts were eliminated by heating to 100° C. 136 Grams of crude product (89.3% of the theoretical yield) were obtained and could be directly used as a flame-proofing agent for fibrous material. A two-fold fractionation via a Vigreux column of 25 cm in length resulted in 94 g of a distillate having a boiling point, under a pressure of 0.05 mm Hg, of from 115° to 118° C and a refractive index $n_{20} = 1.4745$. The product contained, according to gaseous-phase chromatogram and NMR spectrum, 92.5% by weight of the compound of the formula

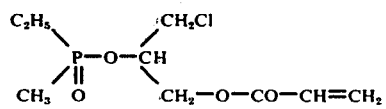

Yield (calculated on the 100% substance): 57.2% of the theory; molecular weight of the 100% compound: 254.66.

EXAMPLE 3

81 Grams (0.536 mol) of a commercial-type 94% methacrylic acid glycidyl ester were added dropwise while cooling within 60 minutes at 90° – 100° C to a mixture of 70 g (0.5 mol) of methyl-propyl phosphinic acid chloride, 0.5 ml of tin tetrachloride and 0.1 g of phenothiazine. After stirring had been continued for 2 hours, the acid number had dropped to 7. After the addition of another 0.15 g of phenothiazine, 19 g of readily volatile contaminants were distilled off at 0.03 torr and at 120° C via a Vigreux column of 25 cm in length. 132 Grams ( = 93.4% of the theoretical yield) of crude product were obtained. This could be used directly for a flame-proof finish on textile fibrous material. A purification by fractionated distillation was possible.

At a boiling point of 125° – 128° C, under a pressure of 0.04 mm Hg, 103 g of a main fraction separated which contained, according to gaseous-phase chromtogram and NMR spectrum, 86.5% of the compound of the formula

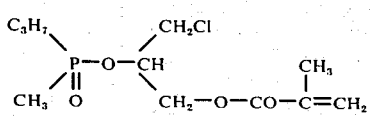

The yield obtained after a single distillation was 89 g = 63.2% of the theoretical yield (calculated on the 100% substance). A further distillation step did practically not increase the degree of purity, presumably owing to a beginning partial decomposition.

The refractive index of the distillate was $n_{20}$ = 1.4704. The molecular weight of the 100 % substance was 282.71.

EXAMPLE 4

112.5 Grams (1 mol) of dimethyl phosphinic acid chloride, 0.1 g of hydroquinone monomethyl ether and 0.1 g of phenothiazine were heated to 70° C, and at this temperature, 138 g (1 mol) of a commercial-type 92.8% acrylic acid glycidyl ester were added dropwise within 50 minutes. Stirring was continued for 3 hours at 70° C, whereupon the acid number dropped to 14. After cooling, the pH value was adjusted to 5 by means of 8 g of a 33% sodium methylate solution, and the methanol was eliminated at 80° C in a water-jet vacuum. The crude product thus obtained could be used directly for a flame-proof finish.

According to the characteristical lines in the NMR spectrum at 3.8, 4.4 and 4.8, the compound of the formula

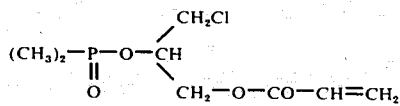

was obtained. The molecular weight of the pure substance was 240.63.

EXAMPLE 5

56.2 Grams (0.5 mol) of dimethyl phosphinic acid chloride, 0.2 g of phenothiazine, 100 g of anhydrous benzene and 2 g of anhydrous tin tetrachloride were mixed, and 69 g (0.5 mol) of a commercial-type 92.8% acrylic acid glycidyl ester were added dropwise at 20° C within 4 hours. By adding 4 g of a 33% solution of sodium methylate in methanol, the pH-value was adjusted to 5, measured with moist Merck-Universal indicator paper, the resulting turbid substance was suction-filtered, and the solvents were distilled off in a water-jet vacuum. A residue of 132 g was obtained which could directly be used as a flameproofing agent for textile fibrous material. The NMR spectrum indicated that the same product as in Example 4 was obtained.

EXAMPLE 6

156 Grams (1.05 mols) of a commercial-type 94% methacrylic acid glycidyl ester were added dropwise at 110° C within 60 minutes to a mixture of 94 g (1 mol) of dimethyl phosphinic acid and 0.1 g of phenothiazine, whereupon an only weak generation of heat was observed. After stirring has been continued for 5 hours at 110° to 115° C, the acid number had dropped to 1.6. After addition of another 0.2 g of phenothiazine, 3 g of contaminants were distilled off at 0.05 torr and at 110° C. The crude product polymerized during a distillation attempt. It could, however, be used directly without purification by distillation for the flame-proof finishing of textiles. The NMR spectrum proved, in the crude product, the presence of the compounds of the formulae

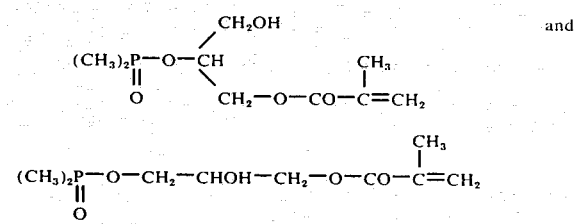

The molecular weight of the pure substance was 236.31.

EXAMPLE 7

145 Grams (1.05 mols) of a commercial-type 92.8% acrylic acid glycidyl ester were added dropwise at 105° C within 60 minutes, while slightly cooling, to 94 g (1 mol) of dimethyl phosphinic acid and 0.1 g of phenothiazine. After stirring had been continued for 6 hours, the acid number had dropped to 3.1. The product polymerized on an attempt to distil it, despite another addition of 0.2 g of phenothiazine and 0.2 g of copper chips. Without distillation, the crude product was nonetheless directly suitable for flame-proof finishes. According to the NMR spectrum, a mixture of the compounds of the formulae

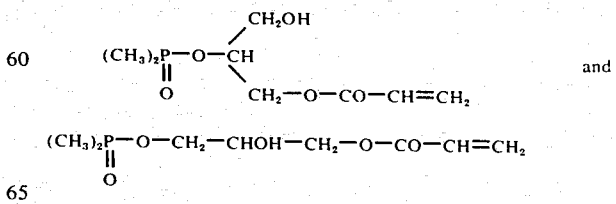

was obtained. The molecular weight of the pure substance was 222.18.

EXAMPLE 8

70.4 Grams (0.55 mol) of a commercial-type 92.8% acrylic acid glycidyl ester were added dropwise at 90° C within 60 minutes to 54 g (0.5 mol) of ethyl-methyl phosphinic acid and 0.1 g of phenothiazine. After stirring had been continued for 10 hours at 100° – 110° C, the acid number had dropped to 2.7.

Yield of crude product: 114 g. It could be directly used as a flame-proofing agent for textile fibrous material.

The NMR spectrum proved the presence of a mixture of substances of the formulae

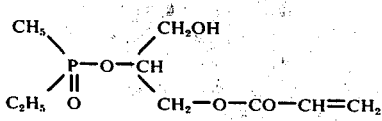

and

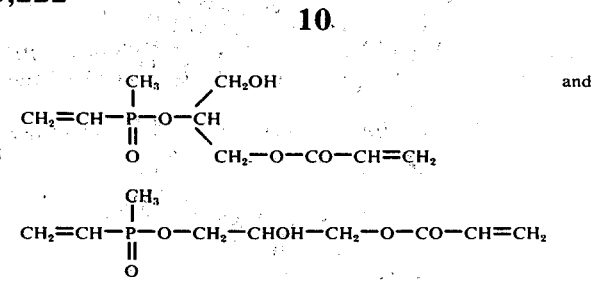

It could be used directly as a flame-proofing agent for textile material.

The molecular weight of the pure isomeric substances was 219.16 ($C_8H_{12}O_5P$).

Molecular weight of the pure substance: 236.21.

EXAMPLE 9

46.5 Grams (0.25 mol) of ethane-1,2-bis-(methyl-phosphinic acid), 0.1 g of phenothiazine and 64 g (0.464 mol) of a 92.8% acrylic acid glydicyl ester were stirred for 5 hours at 115° – 120° C, where-upon the bis-phosphinic acid slowly dissolved. At 90° – 95° C, 29 g (0.5 mol) of propylene oxide were added dropwise within 120 minutes, the mixture was refluxed for 2 hours, and excess propylene oxide and contaminants were eliminated at 1 torr and at 110° C. The residue contained 7.5 g (0.129 mol) of propylene oxide in a chemically linked form. The acid number dropped to 2.

Yield of crude product: 113 g. The NMR spectrum showed the presence of a mixture, presumably consisting of compounds of type Ib

EXAMPLE 11

40.4 Grams (0.3 mol) of a commercial-type 94.9% acrylic acid glycidyl ester were added dropwise at 140° C to 37.2 g (0.2 mol) of 1-bromo-vinyl-methyl phosphinic acid and 0.3 g of semicarbazide hydrochloride. After stirring for only 60 minutes at 140°–150° C, the acid number had dropped to 2.6.

Yield: 77 g of crude product which could be directly used as a flame-proofing agent. The NMR spectrum proved the presence of a mixture of isomeric compounds of the formulae

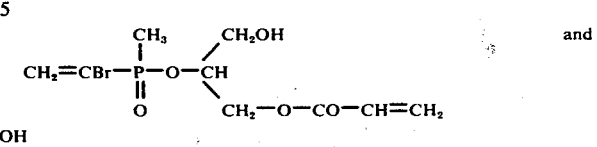

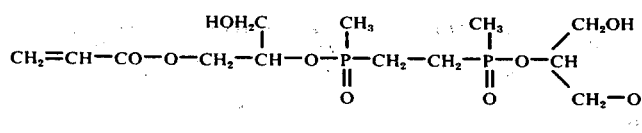

and and the corresponding pure linear compounds Ia as well as mixed types, in which both types Ia and Ib were present. The crude mixture could directly be used as a flame-proofing agent.

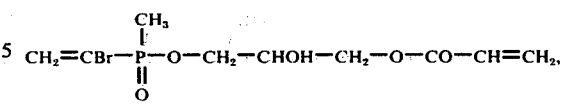

which was insoluble in water.

The molecular weight of the pure isomers was 298.07 ($C_8H_{11}O_5BrP$).

EXAMPLE 10

29.7 Grams (0.22 mol) of a commercial-type 94.6% acrylic acid glycidyl ester were added dropwise at 115° C within 30 minutes to 21.2 g (0.2 mol) of methyl-vinyl phosphinic acid and 0.1 g of phenothiazine. After stirring had been continued for 16 hours at 115° – 120° C, the acid number had dropped to zero.

Yield of crude product: 50 g.

The NMR spectrum proved the presence of a mixture of the compounds of the formulae

EXAMPLE 12

66.9 Grams (0.45 mol) of a 95.7% methacrylic acid glycidyl ester were added dropwise at 120° C within 30 minutes to 66.4 g (0.4 mol) of 2-methoxycarbonyl-ethyl-methyl phosphinic acid and 0.3 g of phenothiazine.

After stirring had been continued for 2 hours at 120° C, the acid number had dropped to 4. Yield of the crude product: 133 g.

The NMR spectrum proved the presence of a mixture of compounds of the formulae

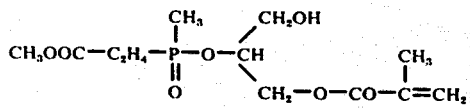

and

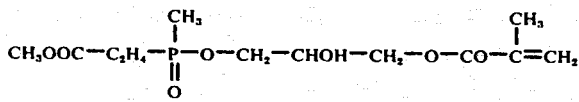

which could be used directly as flame-proofing agent for textile material.

The molecular weight of the pure isomeric substances was 308.27 ($C_{12}H_{21}O_7P$).

I claim:

1. An unsaturated phosphorus compound of the formulae

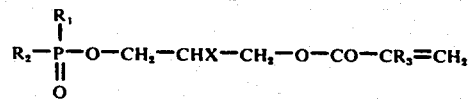

and

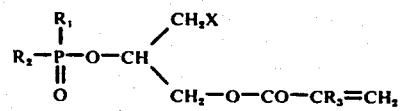

in which $R_1$ is a saturated or unsaturated aliphatic hydrocarbon radical of 1 to 8 carbons which may also carry chlorine, bromine, cyano, $-OR_4$, $-COOR_4$ or $-CON(R_4)_2$, $R_2$ has the same meaning as $R_1$ and additionally is a radical of one of the formulae

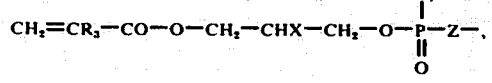

or

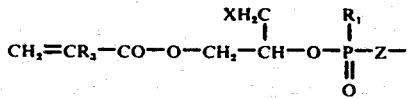

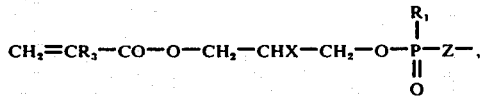

in which Z is a straight or branched chain alkylene of 1 to 8 carbons, phenylene or a xylylene which may carry chlorine, bromine or hydroxy, and Y is a straight or branched chain —O-alkyl of 2 to 8 carbons which may carry chlorine, bromine and/or hydroxy, or is a chlorine, bromine or hydroxy, $R_3$ is hydrogen or methyl, $R_4$ is hydrogen, alkyl of 1 to 8 carbons or alkenyl of 2 to 8 carbons which may carry chlorine, bromine or hydroxy, and X is chlorine, bromine or hydroxy.

2. A compound of claim 1 wherein said hydrocarbon radical has 1 to 4 carbons, said alkylene has 1 to 3 carbons, said xylylene is p-xylylene, said -O-alkyl has 2 to 4 carbons, said alkyl has 1 to 4 carbons, and said alkenyl has 2 to 4 carbons.

3. A compound as claimed in claim 1, wherein $R_1$ is lower alkul, $R_2$ is lower alkyl, lower alkenyl, chloro lower alkyl, bromo lower alkyl, chloro lower alkenyl, bromo lower alkenyl or carbo lower alkoxy lower alkyl, or $R_2$ is a group of the formulae

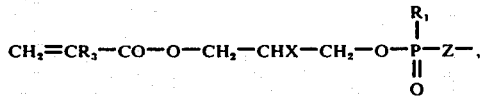

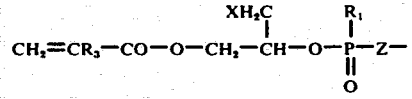

or

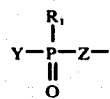

Z is lower alkylene, Y is chlorine, bromine, hydroxy or alkoxy with 2 to 4 carbon atoms substituted by chlorine, bromine or hydroxy, $R_3$ is hydrogen or methyl and X is chlorine, bromine or hydroxy with the proviso that lower means 1 to 4 carbon atoms.

* * * * *